(12) United States Patent
Shaik et al.

(10) Patent No.: US 9,732,018 B2
(45) Date of Patent: *Aug. 15, 2017

(54) PROCESS FOR PRODUCTION OF MIXED BUTANOLS AND DIISOBUTENES AS FUEL BLENDING COMPONENTS

(71) Applicant: Saudi Arabian Oil Company, Dhahran (SA)

(72) Inventors: Kareemuddin M Shaik, Dhahran (SA); Wei Xu, Dhahran (SA); Ibrahim A. Abba, Dhahran (SA); Thamer Mohammed, Dhahran (SA); Hiren Shethna, Dhahran (SA); Kadhim Abbas Mohammed, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 181 days.

This patent is subject to a terminal disclaimer.

(21) Appl. No.: 14/177,818

(22) Filed: Feb. 11, 2014

(65) Prior Publication Data

US 2015/0225320 A1 Aug. 13, 2015

(51) Int. Cl.
*C07C 2/28* (2006.01)
*C07C 29/04* (2006.01)
(Continued)

(52) U.S. Cl.
CPC ............... *C07C 29/172* (2013.01); *C07C 2/28* (2013.01); *C07C 29/04* (2013.01); *C10G 3/42* (2013.01);
(Continued)

(58) Field of Classification Search
CPC .......... C10G 2300/305; C10G 2400/02; C10G 3/42; C10G 50/00; C10L 10/10;
(Continued)

(56) References Cited

U.S. PATENT DOCUMENTS 1,283,435 A 10/1918 Warren
2,875,138 A 2/1959 Altreuter et al.
(Continued)

FOREIGN PATENT DOCUMENTS

CN 1532177 9/2004
CN 1603290 4/2005
(Continued)

OTHER PUBLICATIONS

Matsunaga, Etsuo et al., "Secondary Butyl Alcohol via Direct Hydration", Process Economics review PEP 84-1; May 1985 (PEP Review # 84-2-2). pp. 1-19.
(Continued)

*Primary Examiner* — Latosha Hines
(74) *Attorney, Agent, or Firm* — Leason Ellis LLP

(57) ABSTRACT

A process for simultaneously hydrating and oligomerizing a hydrocarbon feed comprising mixed olefins incudes the steps of: (a) introducing the hydrocarbon feed in the presence of water into a fixed bed; (b) contacting the hydrocarbon feed with a catalyst within said fixed bed reactor, where the catalyst is of the type that hydrates the mixed olefins to form mixed alcohols and oligomerizes at least a portion of the mixed olefins into oligomers to produce a first product stream that includes an organic phase and an aqueous phase; (c) introducing the first product stream into a first separator which separates the organic phase from the aqueous phase; (d) introducing the separated organic phase into a second separator which separates unreacted olefins from mixed alcohols and one or more oligomers which comprise a final product stream; and (e) introducing the separated aqueous phase into a third separator which separates an alcohol-water azeotrope component from water.

23 Claims, 7 Drawing Sheets

(51) Int. Cl.
*C10L 10/10* (2006.01)
*C10L 1/06* (2006.01)
*C07C 29/17* (2006.01)
*C10G 3/00* (2006.01)
*C10G 50/00* (2006.01)

(52) U.S. Cl.
CPC ............... *C10G 50/00* (2013.01); *C10L 1/06* (2013.01); *C10L 10/10* (2013.01); *C07C 2531/08* (2013.01); *C10G 2300/305* (2013.01); *C10G 2400/02* (2013.01); *Y02P 30/20* (2015.11)

(58) Field of Classification Search
CPC .......... C10L 1/06; Y02P 30/20; C07C 29/172; C07C 2/28; C07C 29/04; C07C 2531/08
See application file for complete search history.

(56) References Cited

U.S. PATENT DOCUMENTS

| | | | |
|---|---|---|---|
| 3,203,872 | A | 8/1965 | Baumann |
| 3,328,471 | A | 6/1967 | Kronig et al. |
| 3,981,921 | A | 9/1976 | Bohmholdt et al. |
| 4,087,471 | A | 5/1978 | Bowman et al. |
| 4,214,107 | A | 7/1980 | Chang et al. |
| 4,236,034 | A | 11/1980 | Aoshima et al. |
| 4,476,333 | A | 10/1984 | Neier et al. |
| 4,499,313 | A | 2/1985 | Okumura et al. |
| 4,611,086 | A | 9/1986 | Gueguen et al. |
| 4,902,385 | A | 2/1990 | Osterburg |
| 5,080,691 | A | 1/1992 | Sorensen et al. |
| 5,105,023 | A | 4/1992 | Marler et al. |
| 6,111,148 | A | 8/2000 | Ogawa et al. |
| 6,660,898 | B1 | 12/2003 | Pyhaelahti et al. |
| 7,125,474 | B2 | 10/2006 | Beckmann et al. |
| 7,128,814 | B2 | 10/2006 | Beckmann et al. |
| 7,244,873 | B1 * | 7/2007 | Kleinworth ............... C07C 2/28 208/311 |
| 8,558,036 | B2 | 10/2013 | Xu |
| 2005/0283038 | A1 * | 12/2005 | Kuechler .................. C07C 1/20 585/639 |
| 2013/0104449 | A1 * | 5/2013 | Xu ........................ C10L 1/125 44/452 |

FOREIGN PATENT DOCUMENTS

| | | | |
|---|---|---|---|
| EP | 2374780 | 10/2011 | |
| FI | EP 0994088 A1 * | 4/2000 | ............... C07C 2/08 |

OTHER PUBLICATIONS

Mahajani, S. M. et al., "Extractive hydration of n-butene with solid acid catalysts in the liquid phase and under supercritical conditions" Chemical Engineering Science 56 (2001) 5625-5633.

Miao Sun, et al., "Significant Effect on Acidity on Catalytic Behaviors of Cs-Substituted Polyoxometalates for Oxidative Dehydrogenation of Propone," Applied Catalysis A: General (2008); pp. 212-221.

Catalysis A: General (2008); pp. 212-221.

* cited by examiner

PROCESS FOR PRODUCTION OF MIXED BUTANOLS AND DIISOBUTENES AS FUEL BLENDING COMPONENTS

TECHNICAL FIELD

The present invention relates to a novel process for the production of mixed alcohols (butanols) and butene oligomers. More specifically, the present invention relates to a process for hydrating and oligomerizing a feed stream that includes butene isomers to produce mixed butanols and butene oligomers. The present invention utilizes various process schemes to separate various components formed during the process and the resulting mixed butanols and butene oligomers can be used as fuel blending components.

BACKGROUND

Although hydrocarbon fuels remain as the dominant energy resource for internal combustion engines, alcohols such as methanol and ethanol have also been used as fuels. Ethanol, the primary alcohol fuel, is commonly blended into gasoline in quantities of 5 to 10%. In fact, various fuels being produced today consist primarily of alcohols. For example, E-85 fuel contains 85% ethanol and 15% gasoline, and M-85 fuel has 85% methanol and 15% gasoline. While ethanol possesses excellent octane enhancement properties, there are several drawbacks to its use as a gasoline component, including: energy deficiencies (ethanol provides approximately 39% less energy than gasoline), high blending Reid Vapor Pressure (RVP) (at 10% of blending, the RVP=11 psi), and incompatibility with existing transportation facilities.

Previously, lead (Pb) was added to gasoline to increase its octane rating and thereby improve its antiknock properties. However, the use of lead in gasoline has now been eliminated in most countries for health and environmental reasons. Consequently, methyl-tiary-butyl-ether (MTBE) was commercially introduced as an octane enhancing component of gasoline in the United States and other countries in the late 1970s in order to meet the need for increased octane ratings in the absence of lead. Legal restrictions on the minimum oxygen content of some gasolines—introduced in the 1990s as a means of reducing environmentally harmful exhaust emissions—encouraged a further increase in the concentration of MTBE in gasoline, which, by then, was being blended at up to 15% by volume. While MTBE is still widely used in some countries such as the United Kingdom, its use has been in gradual decline in other regions of the world due to concerns about the harmful effects of MTBE itself. Specifically, its existence in groundwater has led to a decline in its use in the United States, where some states have actively legislated against its use. Thus, to meet today's performance and legal requirements, the fuel industry in the United States is now replacing MTBE with fermented grain ethanol. Producing the necessary quantities of grain ethanol to replace MTBE, however, has proven problematic in specific regions, and the use of ethanol as a gasoline component has other drawbacks as discussed above.

Certain other alcohols (i.e., butanols), as well as butene oligomers (e.g., diisobutenes (DIBs)) can be used as combustible neat fuels, oxygenate fuel additives, or constituents in various types of fuels. The BTU content of butanols and diisobutenes is closer to the energy content of gasoline than either ethanol or methanol. Butanols have been thought of as second generation fuel components after ethanols. In particular, 2-butanol and t-butanol can be advantageous fuel components, as they have blending octane sensitivities and energy densities comparable to those of MTBE and have been shown to have lower RVP at 15% concentrations relative to comparable ethanol blends. Likewise, DIB is a non-oxygenated fuel component with several advantages over other fuel additives. For instance, DIBs have better anti-knock quality, higher RON, and higher energy content compared with MTBE, as well as a lower RVP than ethanol, butanols, or MTBE.

Butanols can be produced via the hydration of butenes, a process that typically utilizes an acid catalyst. While the production of butanols via hydration of butenes is a commercially important process, it is typically very costly. DIBs are produced via the oligomerization/dimerization of butenes, in particular isobutene. The dimerization of isobutene is also generally performed using acid catalysts, such as sulfuric acid and hydrogen fluoride; however, these catalysts tend to be highly corrosive in nature.

Butanols and DIBs provide certain advantages over other existing fuel components. For instance, the combination of butanols and DIBs as a fuel additive would lead to enhanced octane sensitivity, energy density, and RON, as well as decreased RVP in gasoline. Only recently have there been any processes for converting mixed olefins into alcohols—especially butenes into butanols—while also dimerizing part of the mixed olefins feed into oligomers such as DIBs without requiring the costly separation of either mixed butenes isomers in the feed or the mixed butanol isomers in the product. Still, inefficiencies exist in current processes for the contemporary hydration and dimerization of mixed butenes.

U.S. Patent Application No. 2013/0104449 (the '449 publication) is a method for contemporaneously dimerizing and hydrating a hydrocarbon feed containing butene, resulting in the production of alcohols and DIBs. While the '449 publication addresses the need for simultaneously hydrating and oligomerizing a mixed butene feed to produce butanols and DIBs, the process in '449 publication is limited in its ability to 1) separate the butanol/DIB products from water, 2) produce high-purity, on-specification butanols, and 3) convert butenes to butanols and DIBs in a single pass. These limitations lead to increased costs, specifically the costs associated with recycling unreacted butenes back to the reactor to increase product yield and costs associated with further separating the product from water to produce higher purity butanols and DIBs.

Thus, there is a need for alternative gasoline oxygenates that possess comparable RON enhancement properties and a higher energy content than MTBE and ethanol, but that also eliminates the environmental and compatibility concerns of MTBE and ethanol. There is also a need for alternative fuel additives that lower the RVP of fuel in the absence of MTBE. Finally, there is a need for a process that not only allows for the contemporaneous hydration and oligomerization of mixed butenes to alcohols and oligomers—namely butanols and DIB—but also increases the conversion rate of butenes and produces higher purity product streams.

SUMMARY

The present invention is directed to a process encompassing various schemes to produce high-purity, on-specification mixed butanol products, which are potential replacement oxygenates for MTBE and ethanol as fuel additives. More specifically, this invention relates to a process for producing mixed butanols—preferably, 2-butanol and t-butanol—and DIBs from the hydration and oligomerization of a mixed butene feed. The mixed butanols and DIBs are produced simultaneously in a fixed bed reactor via the hydration of all butene isomers and the oligomerization (dimerization) of at least one butene isomer (e.g., isobutene), respectively.

In one embodiment, the process scheme consists of a fixed bed reactor, a high-pressure separator, a low-pressure separator, a debutenizer, and an azeotropic distillation column, which allows for the production of high-purity mixed butanols and DIBs while minimizing product loss.

In another embodiment, a pervaporation membrane is integrated into the scheme to enhance separation of the products from water. In yet another embodiment, a two column entrainer system is added in the place of an azeotropic distillation column to assist in the extraction of mixed butanols from the azeotropic mixture. In yet another embodiment, a purge capture feature is incorporated into the process to enhance the product yield.

This invention provides a distinct advantage over other hydration and oligomerization processes, as it allows for 1) the increased single pass conversion of mixed butenes to mixed butanols and butene oligomers, and 2) a higher purity product stream that consists of less water than product streams of prior hydration/oligomerization processes. Thus, the ability to increase the single pass conversion of butenes to products, and produce a high-purity, on-specification product stream that consists of less water compared with the prior art results in a process that is more efficient and cost-effective than its predecessors. Additionally, the product stream, which consists of mixed butanols and DIBs, is a product that possesses superior gasoline blending properties.

BRIEF DESCRIPTION OF THE DRAWING FIGURES

A more complete understanding of the invention and its many features and advantages will be attained by reference to the following detailed description and the accompanying drawing. It is important to note that the drawing illustrates only one embodiment of the present invention and therefore should not be considered to limit its scope.

DETAILED DESCRIPTION OF CERTAIN EMBODIMENTS

Figure 1:
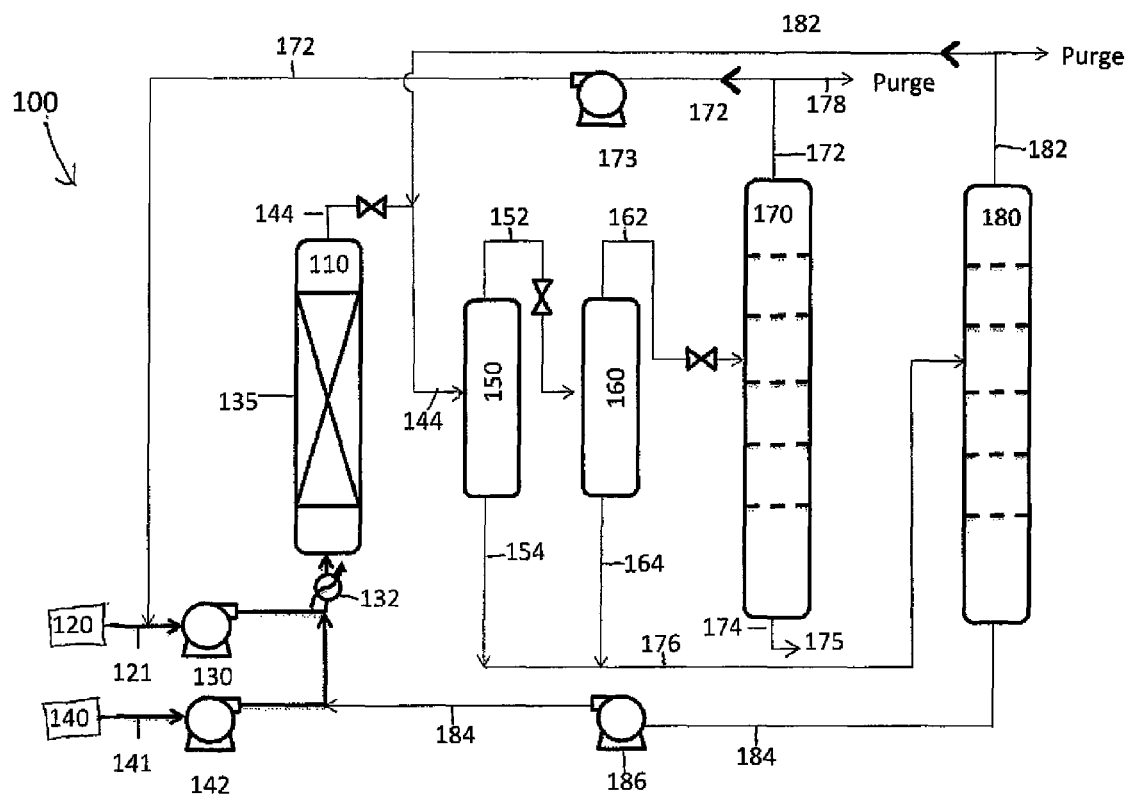
FIG. 1 shows a diagram of a process in accordance with a first embodiment of the present invention.

As mentioned hereinbefore, the prior art includes several processes for the hydration and oligomerization of mixed butenes into alcohols and butene oligomers. However, until now, there have not been any processes for converting a mixed olefin feed (e.g., mixed butene feed) into alcohols (e.g., butanols) and butene oligomers that have a particularly high single-pass conversion rate, nor have there been processes that produce high-purity butanol/DIB product streams.

The present invention overcomes the deficiencies and limitations of the prior art and is directed to a process for the hydration and oligomerization of mixed butenes to produce a mixed butanols and DIB product, which can be used as a superior gasoline blending additive. As described herein, the process of the present invention allows for increased single-pass conversion of mixed butenes to mixed butanols and DIBs, and improved removal of water from the final product, thereby allowing for a final product that is of higher yield and greater purity.

Mixed Olefins (Butenes)

Mixed butenes have four structural isomers: 1-butene, 2-cis-butene, 2-trans-butene, and isobutene. Optionally, other low olefins, such as propylene and ethylene, can also be present in the feed as described below.

Diisobutenes (DIBs) or Isooctenes

Diisobutenes include two isomers of 2,4,4-tri-methyl-1-pentene and 2,4,4-trimethyl-2-pentene.

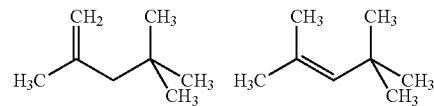

Mixed Butanols

Mixed butanols include at least two of the following compounds: 1-butanol, 2-butanol, t-butanol, and isobutanol. Preferred embodiments of the present invention include only 2-butanol and t-butanol as described below.

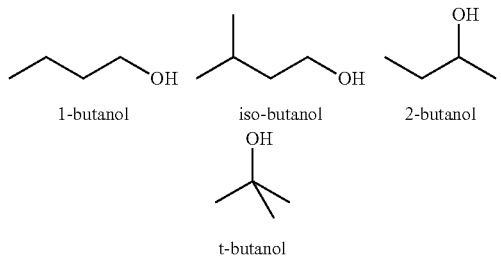

Hydration of Mixed Butenes

Processes for the hydration of butenes to butanols are commercially important reactions as the products have several important industrial applications. Generally, the hydration of mixed butenes is selected to only produce 2-butanol and t-butanol; however, the formation of other compounds is possible. Mixed butanols, primarily 2-butanol and t-butanol, can be used as oxygenative-type premium gasoline additives.

Isobutene+water⇌t-butanol
n-butene+water⇌2-butanol

Other possible products that can be derived from the hydration of mixed butenes include but are not limited to etherification products of butanols and butenes or butanols itself. Butanols generally have good gasoline octane blending characteristics and can be used in combination as petroleum additives with other oxygenates, such as ethanol and MTBE.

Oliqomerization (Dimerization)

Oligomerizations of mixed butenes as described herein include oligomerizations of all butene isomers, preferably oligomerizations of isobutene and more preferably, the dimerization of isobutene. The oligomerization fraction can be extremely rich in dimers (isooctenes or DIBs), and can be added as such to the gasoline cuts to give a very high quality gasoline.

Major compounds that can be derived from the oligomerization of mixed butenes include but are not limited to: diisobutenes (DIBs), tri-isobutenes, dimer of isobutene and n-butenes, and trimer of isobutene and n-butenes can all be derived from the oligomerization of mixed butenes. It will be appreciated by one of skill in the art that other products can be formed. As is known, DIB is a non-oxygenative fuel component with many advantages as a blending agent, such as higher RON, higher octane sensitivity or better anti-knock quality, higher energy content compared to MTBE and alkylates, and/or lower RVP than MTBE and ethanol.

Dimerization of Isobutene

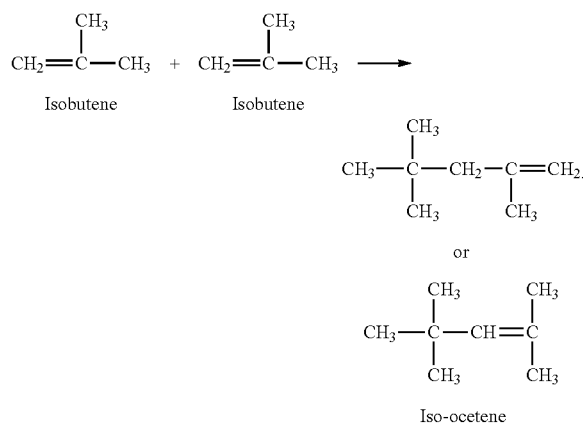

The Present Hydration/Oligomerization Process

As described herein, processes for production of mixed butanols (mixed alcohols) and butene oligomers from a hydrocarbon feed (mixed olefin feed) are provided as embodiments of the present invention. Additionally, processes for producing fuel compositions that include alcohols and oligomers prepared from the n-butenes are also provided as embodiments of the present invention.

In one embodiment of the present invention, a process for producing alcohols and oligomers from mixed olefins is provided. More specifically, the process is one in which mixed olefins are simultaneously hydrated and oligomerized in the presence of water. A product stream that includes alcohols and butene oligomers is formed. In certain embodiments, the mixed olefin feed consists of a mixed butene feedstock and the product stream includes mixed butanols and DIBs. In one embodiment, the product stream that includes mixed butanols and DIBs and can be combined with a fuel component to produce a fuel composition. The fuel component of the fuel composition can be selected from gasoline, diesel, jet fuel, aviation gasoline, heating oil, bunker oil, or combinations thereof. In certain embodiments, the resultant fuel composition will have increased RON and reduced RVP, without the presence of other chemicals that can have deleterious effects on the environment.

The source of the mixed olefin (e.g., mixed butene) stream can encompass any number of different sources of feedstocks (streams) that are suitable for use in the present invention. In some embodiments, the mixed olefin stream can be a refinery gas stream. In one embodiment, the mixed olefin stream can simply be a mixture of light olefins.

Various types of olefins can be included in the mixed olefin stream. As mentioned herein, in certain embodiments, the mixed olefin stream can include a mixed butene stream. In another embodiment, the mixed olefin stream can include pentenes, hexenes, propylene, n-butene, 2-butene, isobutene, olefins having more than 6 carbons with at least two butenes, or combinations thereof. Other olefins that can be used in accordance with other embodiments include ethylene, propene, butenes, pentenes, or other higher olefins. It will be understood that other suitable sources for the mixed olefin stream and types of olefins can be used so long as they are suitable for the intended application described herein and achieve a product stream having the desired characteristics that are set forth herein. In yet another embodiment, the mixed butene feed used in the present invention contains the four butene isomers in varying quantities as set forth in Example 1 below.

Most commercialized butene hydration processes utilize pure feeds of either 1-butene or isobutene, or mixed feeds for selective isobutene hydration. The process conditions are typically selected to maximize the yield of either 2-butanol or t-butanol. Because both 2-butanol and t-butanol are valuable oxygenates and octane enhancers for fuels, certain embodiments of the present invention utilize a system that is effective for the production of 2-butanol and t-butanol.

Regarding the oligomerization of butenes, different butene isomers have different activities toward dimerization or oligomerization. For example, it is generally difficult for n-butenes to form the correspondent dimers or oligomers. In contrast, isobutene is predisposed to being dimerized or oligomerized. In accordance with one embodiment of the present invention, the present process is such that a portion of the isobutene in the feed is selectively oligomerized (dimerized) in the fixed bed reactor to form the two isomers of DIB. Thus, in one embodiment, the resultant product stream includes the two isomers of DIBs, 2-butanol, and t-butanol.

Similarly, in regards to the hydration of butenes, the butene isomers vary in their hydration reaction rates. Specifically, the hydration reaction rates for both 2-cis and 2-trans-butene are significantly lower than that of 1-butene. Thus in accordance, with one embodiment of the present invention shown in FIG. 6, an isomerization unit is included in the system to convert 2-butenes into 1-butenes. The conversion of 2-butene isomers to 1-butene isomers can considerably enhance the hydration reactions, thereby increasing the single-pass conversion of mixed butenes to butanols.

As described herein, the catalyst systems of the present invention are configured to perform the intended functions, namely, the hydration and oligomerization of mixed butenes, within one fixed bed reactor. It will be appreciated that the amount of catalyst can vary depending upon the mixed olefin stream being sent to the process. It will be appreciated that any number of suitable catalysts can be used for the hydration and oligomerization reactions so long as the catalyst operates in the manner described herein and achieves the intended objectives. Exemplary catalyst systems are described below.

In accordance with the present invention and as described in detail below and shown in the various figures, once the hydration and oligomerization (dimerization) reactions have occurred, various combinations of systems may be used to separate the product stream from the byproducts and unreacted olefins. In one embodiment, the product stream is first sent from the fixed bed reactor to a high-pressure separator, where the organic phase of the product stream containing unreacted mixed butenes and extracted mixed butanols is separated from the aqueous phase of the product stream, which is saturated with mixed butanols. The organic phase is then sent to a low-pressure separator where water (leftover aqueous phase) is removed from the product stream. The combined high and low-pressure separators can be considered to be a "first separator" as set forth in the claims.

In the embodiment illustrated in FIG. 1, after passing through the low-pressure separator, the organic phase is sent to a debutenizer column (a "second separator") where the unreacted butenes are removed from the final product stream and recycled back to the fixed bed reactor. In some embodiments, the aqueous phase is sent from the high- and low-pressure separators to an azeotropic distillation column (a "third separator"). There, the alcohol-water azeotrope is distilled out of the aqueous phase and recycled back to the high-pressure separator for further recovery of alcohols (butanols), while the water is recycled upstream of the fixed bed reactor. Recycle pumps can be used to re-pressure recycled unreacted butenes and recycled water prior to their return to the system. In some embodiments, part of the alcohol-water azeotrope from the azeotropic distillation column and part of the unreacted butene stream from the debutenizer are purged to reduce inert build-up in the system ("purge streams").

FIG. 1 illustrates one exemplary system 100 for performing the hydration and oligomerization of mixed olefins (butenes) in a process in accordance with a first embodiment of the present invention. FIG. 1 likewise shows an exemplary flow scheme. As described herein, at least the fixed bed reactor has an associated catalyst, and the remaining parts of the system 100 have associated equipment to produce the intended products.

The system 100 includes a fixed bed reactor 110 that serves as both a hydration reactor and an oligomerization reactor.

The reactants are delivered to the fixed bed reactor 110 in the following manner. A source of feedstock (e.g., a mixed olefin feed and more particularly, a mixed butene feed) is identified at 120 and is fluidly connected (e.g., by means of a fluid conduit 121 (such as a pipe)) to the fixed bed reactor 110. Before entering an inlet of the fixed bed reactor 110, the feedstock passes through a first compressor 130 and a heat exchanger 132 that are disposed along the conduit 121 between the source of feedstock 120 and the hydration/oligomerization reactor 110. The heat exchanger 132 is located downstream of the compressor 130. A source of water is identified at 140 and is fluidly connected to conduit 121 by means of conduit 141. The water passes through a second compressor 142 disposed along conduit 141 before entering an inlet of fluid conduit 121. The water, after entering fluid conduit 121, also passes through heat exchanger 132 and then enters the fixed bed reactor 110 along with the feedstock. The reactants can enter the reactor 110 in either an upflow or downflow direction.

The compressors 130 and 142, and the heat exchanger 132 are configured to adjust the pressure and temperature, respectively, of the feedstock and the water prior to their entry into the fixed bed reactor 110 and thus also control the reactor pressure and temperature. In one exemplary embodiment, the fixed bed reactor conditions are a pressure between about 10 bar and about 70 bar and a temperature between about 100° C. and about 160° C. Accordingly, the first compressor 130 and second compressor 142 serves to compress the mixed butene feed stream and the water stream, respectively, to between about 10 bar and about 70 bar and the heat exchanger 132 serves to adjust the temperature of this mixture to between about 100° C. and about 160° C.

The fixed bed reactor 110 is configured to perform hydration and oligomerization of the feedstock introduced therein in the presence of water and under the operating conditions set forth above. The fixed bed reactor 110 can be in the form of a single stage reactor having an inlet connected to the conduit 121 to receive the feedstock 120. Within the reactor 110, a catalyst 135 capable of initiating hydration and oligomerization reactions is contained. For example, the catalyst 135 can be located in one or more regions of the reactor 110.

As described below in greater detail, the catalyst 135 is of a type which hydrates the mixed olefin feedstock and oligomerizes at least a portion of the mixed olefin feedstock. More specifically, the catalyst 135 is of a type and is selected so as to cause the oligomerization (dimerization) of a portion of the isobutene isomers (in the olefin feedstock) to DIBs, while the remaining mixed butenes are hydrated to butanols including the hydration of isobutene to form tert-butanol). As a result, the fixed bed reactor 110 simultaneously hydrates the mixed butenes to form mixed butanols and selectively oligomerizes (dimerizes) a portion of the isobutene isomers to DIBs, and thus, the final product stream includes mixed butanols and DIBs.

In one embodiment, the hydration and oligomerization catalyst comprise an acidic catalyst, such as ionic exchange resins (catalysts). Alternatively, the oligomerization catalyst and/or the hydration catalyst comprise substituted/non-substituted heteropoly acids or zeolites or any acidic solid acids. For example, a heteropoly acid (cesium substituted) can be prepared according to a process described in Miao Sun, et al., "Significant Effect on Acidity on Catalytic Behaviors of Cs-Substituted Polyoxometalates for Oxidative Dehydrogenation of Propone," *Applied Catalysis A: General* (2008); pp. 212-221, which is hereby incorporated by reference in its entirety. Commonly owned U.S. patent application Ser. No. 14/091,137, which is hereby incorporated by reference in its entirety, sets forth catalysts that can be used as catalysts for use in the present invention. The oligomerization catalyst and hydration catalyst can be the same or they can be different catalysts.

Other catalyst system can be used so long as they achieve the objectives stated herein.

The resulting product stream containing mixed butanols and DIBs exits the fixed bed reactor 110 via a conduit 144 and is introduced to a high-pressure separator 150. In the high-pressure separator 150, the organic phase containing unreacted mixed butenes along with extracted mixed butanols is separated from the aqueous phase saturated with mixed butanols. The organic phase is removed from the high-pressure separator through conduit 152, while the aqueous phase is removed from the high-pressure separator 150 through conduit 154. The organic phase, through conduit 152, is then introduced to a low-pressure separator 160 for removal of additional water (i.e., removal of additional aqueous phase). The organic phase (unreacted butenes and extracted butanols) then exits the low pressure separator via conduit 162, and the water (aqueous phase) is removed from the low-pressure separator via conduit 164. As mentioned herein, the combined high and low-pressure separators can be considered to be a first separator in the context of the claims.

First Separation Scheme

The organic phase, via conduit 162, is then introduced to a debutenizer column 170, where unreacted mixed butenes are separated from a product stream. The debutenizer column can be considered to be a second separator in the context of the claims. As is known, a debutenizer is a type of fractional distillation column used to separate butenes from other components during the refining process. Distillation is the process of heating a liquid to vapor and condensing the vapors back to liquid in order to separate or purify the liquid. Fractional distillation, as occurs in a debutenizer, is the separation of a fraction—a set of compounds that have a boiling point within a given range—from the rest of the mixture.

The unreacted butenes exit the debutenizer column 170 via conduit 172, and the product stream exits the debutenizer column via conduit 174 to make the final product identified at 175. It will be appreciated that this final product 175, which can be considered to be a product stream of RON enhanced mixed butanols and DIBs, can then undergo additional processing and/or transportation to another site, such as a storage site.

Most of the unreacted butenes, via conduit 172, are then recycled back to the fixed bed reactor 110 by way of conduit 121 for further processing in the reactor 110. A recycle pump 173 is disposed along conduit 172 to re-pressurize the unreacted butenes prior to their recycle to conduit 121 and the fixed bed reactor 110. A portion of the unreacted butenes exiting the debutenizer 170 into conduit 172 is preferably introduced to conduit 178, through which they are purged from the system 100.

The aqueous phases exiting the high-pressure separator 150 via conduit 154 and the low-pressure separator 160 via conduit 164 are both introduced into conduit 176, through which they are transported to an azeotropic distillation column 180. The azeotropic distillation column 180 can be considered to be a third separator in the context of the claims. In the azeotropic distillation column 180, the alcohol-water azeotrope is distilled out of the aqueous phase and recycled back to the high-pressure separator via conduit 182 to further recover the alcohols (butanols). As mentioned above, a part of the alcohol-water azeotrope recovered from column 180 can be purged as shown in FIG. 1 by being diverted from conduit 182. Water exits the azeotropic distillation column via conduit 184, through which it is introduced to conduit 141 and eventually recycled back to conduit 121 and introduced into the fixed bed reactor 110. A recycle pump 186 is disposed along conduit 184 to re-pressurize the water prior to its recycling to conduit 141 and the fixed bed reactor 110.

As mentioned above, other separation techniques can be used as described below. In FIGS. 2-6, like elements are numbered alike and the discussion of FIGS. 2-6 is focused on the differences between the separation techniques to enhance the yield and purity of the final product.

Second Separation Scheme

Figure 2:
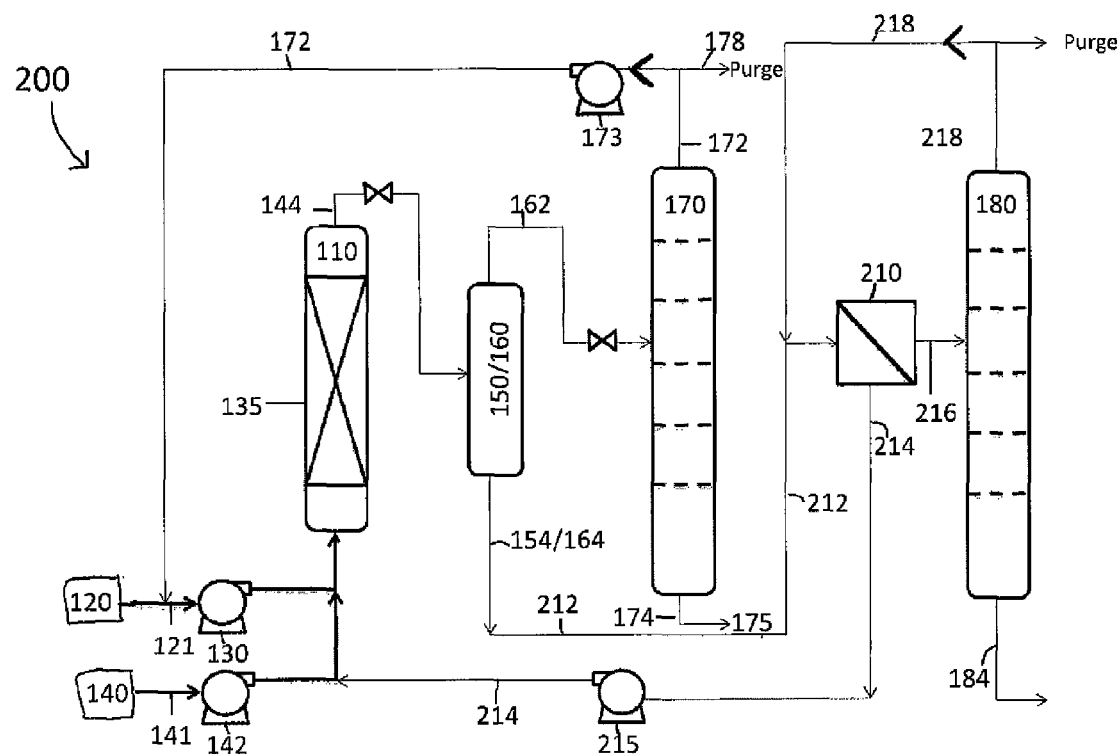
FIG. 2 shows a diagram of a process in accordance with a second embodiment of the present invention.

FIG. 2 illustrates a second separation scheme 200 that includes a pervaporation membrane system 210 that is added to the system 100 directly upstream of the azeotropic distillation column 180 such that water is substantially removed from the aqueous phase before it is sent to the azeotropic distillation column 180.

In FIG. 2 the high and low pressure separators 150, 160 are indicated as a single unit for ease of illustration and it will be understood that the high and low pressure separators 150, 160 are in the form of two separate separators along with separate feed conduits (pipes, lines, etc.) as illustrated in FIG. 1.

From the low pressure separator 160, a conduit 212 carries the aqueous phase to the pervaporation membrane system 210. A short conduit can fluidly connect the conduit 212 to an inlet of the pervaporation membrane system 210. An outlet conduit 214 is fluidly connected to the system 210 and carries the separated water back to line (conduit) 141 for delivering the water back to the reactor 110 for further processing.

The output (aqueous phase) of the pervaporation membrane system 210 is delivered through conduit 216 to the column 180 where the aqueous phase is processed in the manner discussed above with respect to FIG. 1.

The addition of the pervaporation membrane 210 enhances the performance of the azeotropic distillation column 180 to ensure that the water content of the final product meets desired, predefined specifications. Additionally, the alcohol-water azeotrope that is distilled out of the column 180 through conduit 218 is recycled to the pervaporation membrane system 210.

The pervaporation membrane assists in altering the azeotropic mixture composition such that the butanol product can be extracted from the column 180 bottoms while extracting the azeotropic mixture from the 180 tops that will be recycled back to the pervaporation membrane. The composition of the streams around 180 are provided in Table 2. Stream 184 will be mixed with stream 175 to get the final product.

Third Separation Scheme

Figure 3:
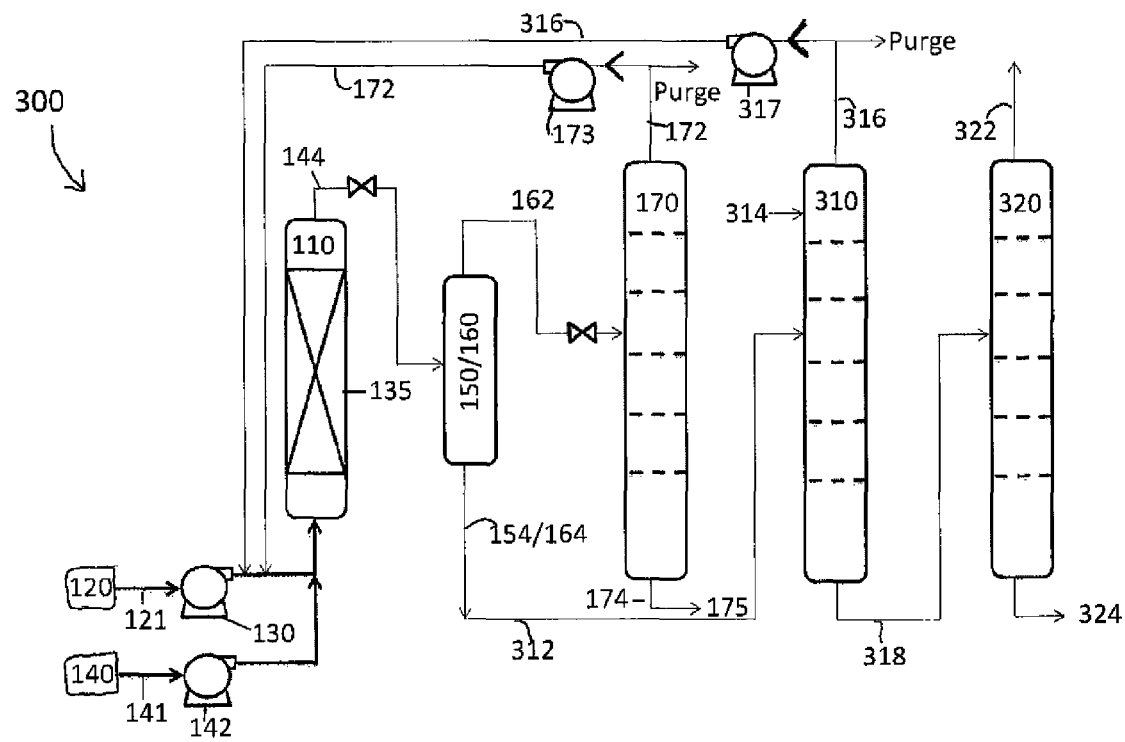
FIG. 3 shows a diagram of a process in accordance with a third embodiment of the present invention.

FIG. 3 illustrates a third separation scheme 300 in which the azeotropic distillation column 180 of FIG. 1 is replaced by a double column entrainer system. The system consists primarily of a contactor column 310 downstream of the debutenizer 170 and a solvent regenerator column 320 downstream of the contactor column 310. A conduit 312 carries the aqueous phase from the high and low separators 150, 160 to an inlet of the contractor column 310.

In one embodiment, 1,3,5 Trimethyl benzene is used as an entrainer (solution), which is introduced into the contactor column 310 through a conduit 314 and helps to absorb the mixed butanols (that are in the aqueous phase) and DIBs, thereby separating them from the unreacted water. The butanols and DIBs dissolve in the entrainer solution. The mixed butanols and DIB product that are dissolved in the entrainer are removed from the contactor column 310 via an outlet conduit 318 and are sent to the solvent regenerator column 320. The unreacted water flows out of the contractor column 310 through a conduit 316 and can be disposed of or otherwise processed.

In the solvent regenerator column 320, the mixed butanols and DIB product stream is removed, and the entrainer (the 1,3,5 Trimethyl benzene solvent) is regenerated and recycled back to the contactor column 310. In FIG. 3, the entrainer exits the column 320 through a conduit 324 and this conduit can thus be directed back to the contractor column 310. The mixed butanols and DIB are removed from the column 320 though a conduit 322 and can be routed to a desired location for further processing, storage, etc.

Fourth Separation Scheme

Figure 4:
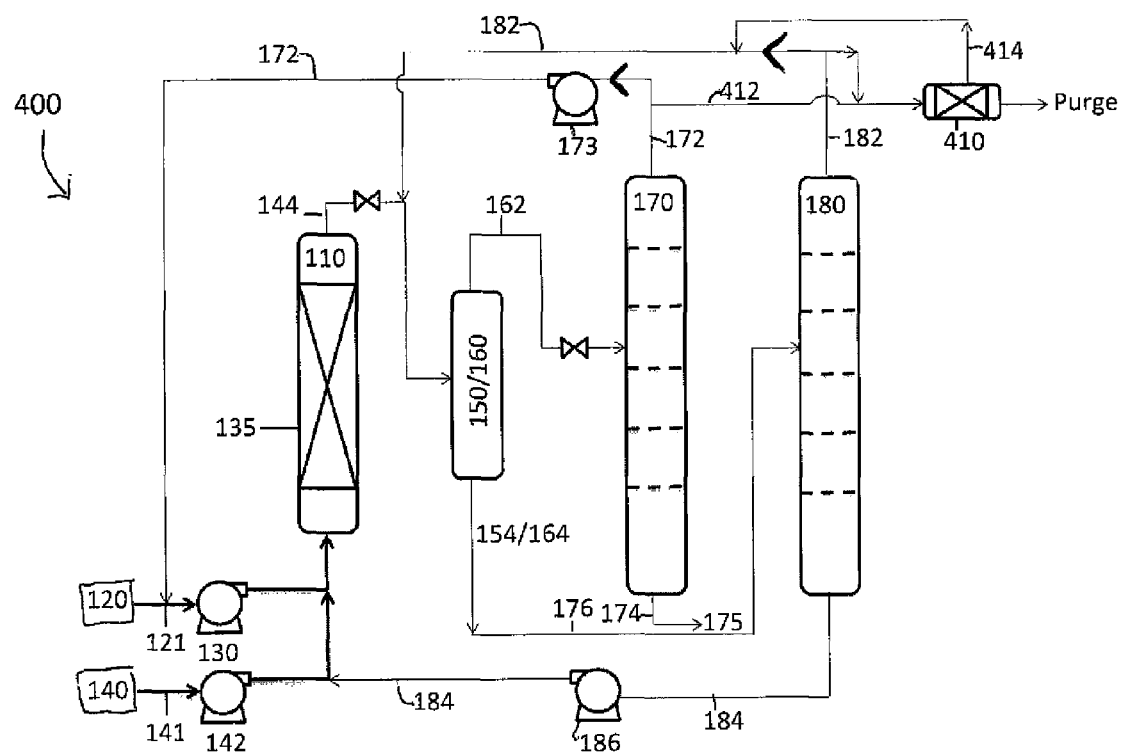
FIG. 4 shows a diagram of a process in accordance with a fourth embodiment of the present invention.

FIG. 4 illustrates a fourth separation scheme 400.

In the embodiment illustrated in FIG. 4, a small fixed bed hydration reactor 410 is added to the system to further increase the butanol yield of the system. The small hydration reactor 410 is located downstream of the debutenizer 170 such that a small portion of unreacted butenes from the debutenizer 170 are sent to the small hydration reactor 410 via conduits 172 and 412, while a majority of the unreacted butenes is recycled back (via conduit 172 and under the action of pump 173) to the main fixed bed reactor 110 to prevent build-up of inert iso-butane and n-butane in the system.

The aqueous phase from the high and low separators flows through conduit 176 to the azeotropic distillation column 180.

Similar to the main reactor, the small bed hydration reactor 410 includes a hydration catalyst for hydrating a portion of the unreacted butenes. The catalyst in the small bed hydration reactor 410 can be one of the ones mentioned within respect to the main fixed bed reactor 110 or can be another one.

In the small bed hydration reactor 410, much of the unreacted butenes in the purge stream, that would otherwise be vented, are hydrated to create butanols, which are then recycled to the high pressure separator 150 via conduits 414, 182. Any unreacted components left in the small bed hydration reactor 410 are then purged from the system. The space velocity of the small bed hydration reactor 410 is significantly lower than that of the main fixed bed reactor 110 to increase the overall mixed butenes conversion rate and to recover as much of the unreacted mixed butenes as possible. The overall build-up of inert compounds such as butane isomers can be substantially reduced by optimizing the use of the small bed hydration reactor 410. The mixed butanols produced in the small bed hydration reactor 410 are recycled to the high-pressure separator 150 by means of conduits 414, 182, while unreacted components are purged. As in FIG. 1, the majority of the alcohol-water azeotrope recovered from column 180 is delivered back to the high pressure separator 150 via conduit 182.

Fifth Separation Scheme

Figure 5:
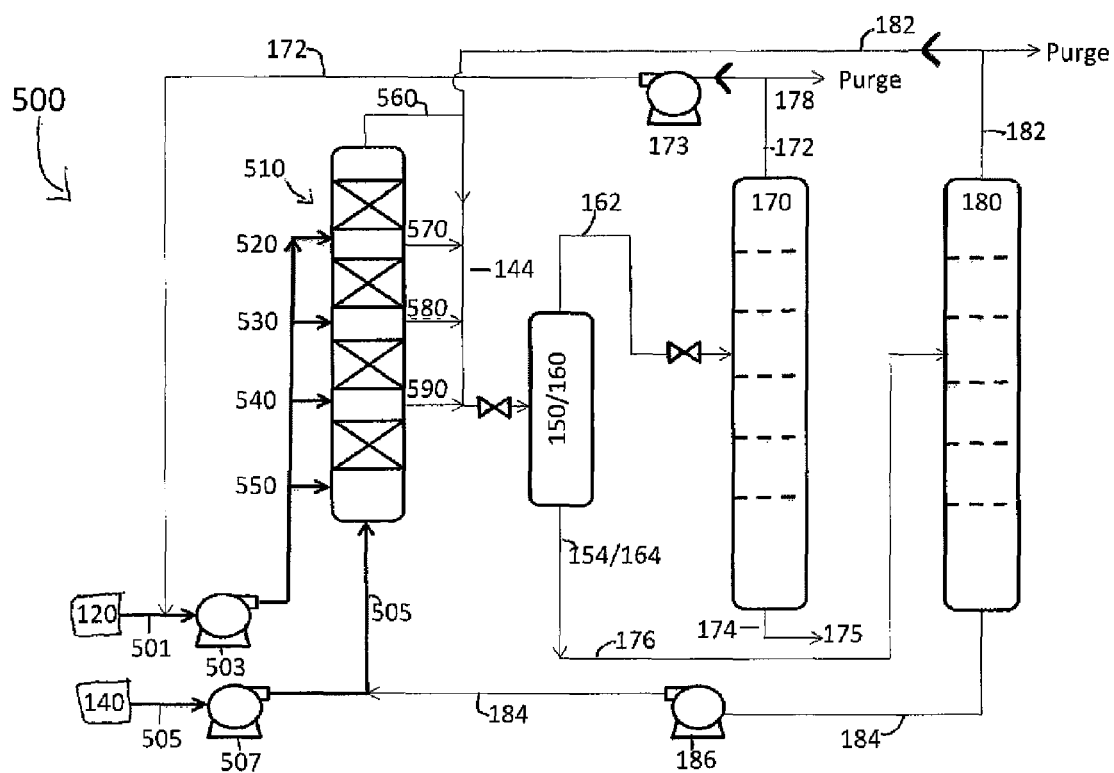
FIG. 5 shows a diagram of a process in accordance with a fifth embodiment of the present invention.

FIG. 5 illustrates a fifth separation scheme 500. In scheme 500, the feed source 120 is connected to a multi-stage reactor 510 by a conduit 501 which includes compressor 503 and a conduit 505 connects the water source 140 to the reactor 510 which includes a compressor 507.

In the embodiment illustrated in FIG. 5, the multi-stage reactor 510 can replace the main fixed bed reactor 110 in the system 100. The different stages of the multi-stage reactor 510 each have an intermittent feed supply (i.e., a conduit segment 501) and product separation modules to enhance the single-pass mixed butenes conversion. More specifically, each stage of the reactor 510 has an entrance for their respective feeds and an exit for their respective products, and each of the product streams is then be sent to the high-pressure separator 150. In FIG. 5, there are four inlet conduits (entrances) 520, 530, 540, 550 (connected to the line/conduit 501) and there are associated exits 560, 570, 580, 590 which correspond to the respective three stages.

The overall single-pass conversion rate is significantly increased with the use of the multi-stage reactor 510, thereby reducing the recycling flow rate and the capital costs of the equipment. In a preferred embodiment, there are three stages in the multi-stage reactor 510; however, in other embodiments, more stages can be employed to further increase the single-pass conversion rate. In yet another embodiment, a purge recovery scheme (See, FIG. 4) can also be employed in conjunction with a multi-stage reactor to enhance product recovery.

Sixth Separation Scheme

Figure 6:
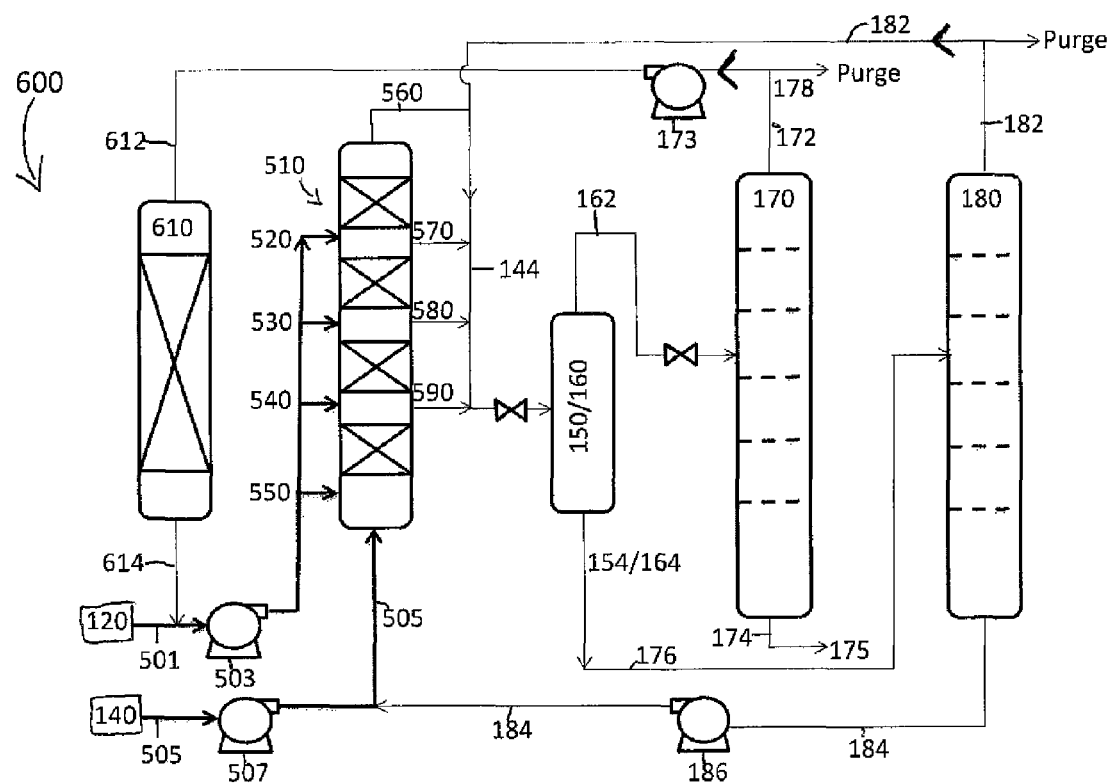
FIG. 6 shows a diagram of a process in accordance with a sixth embodiment of the present invention.

FIG. 6 illustrates a sixth separation scheme 600. In this sixth separation scheme, the system performance is enhanced with a 2-butenes to 1-butenes isomerization unit 610. The isomerization unit 610 is configured such that 2-butenes are converted into 1-butenes prior to entering the multi-stage reactor 110. As shown, the unit 610 includes an exit conduit 614 that is in fluid communication with the conduit 501 for delivering 1-butenes to the reactor 510.

An inlet of the unit 610 is fluidly connected to a conduit 612 which connects to the debutenizer 170 and receives the unreacted butenes therefrom.

Because the hydration reaction rate of 1-butenes is significantly higher than that of 2-butenes, the addition of a "2-butene to 1-butene" isomerization unit further enhances the single-pass conversion rate of the mixed butene feed since the concentration of 1-butenes in the feedstock is increased, while the concentration on 2-butenes is decreased.

Seventh Separation Scheme

Figure 7:
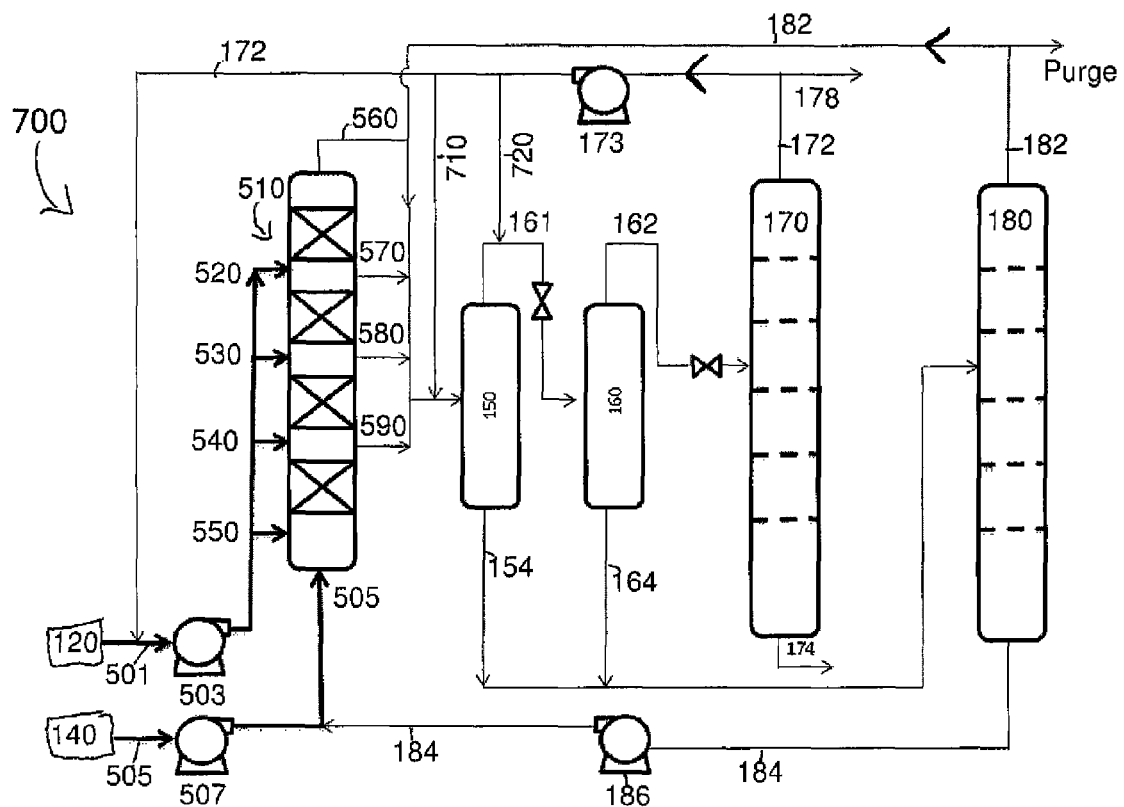
FIG. 7 shows a diagram of a process in accordance with a seventh embodiment of the present invention.

FIG. 7 illustrates a seventh separation scheme 700. In scheme 700, a multi-stage reactor 510 (as also depicted in FIG. 5) is utilized. Additionally, conduit 172 (used to recycle unreacted butenes from the debutenizer 170 back to the multi-stage reactor 510), is also connected to conduits 710 and 720, which can be used to divert a portion of the unreacted butenes back to the high pressure separator 150 and low pressure separator 160, respectively. The use of the multi-stage reactor 510, as in the fifth separation scheme, increased the overall single-pass conversion rate. In the fifth scheme, the recycling flow rate and the capital costs were also reduced; however, in some cases, the reduction in recycling flow rate can impact the efficiency of butanol extraction from the recycled butenes. Thus, the addition of conduits 710 and 720 in the seventh scheme increases the flow rate of the recycled butenes, thereby enhancing the butanol extraction of the system and ultimately keeping the butanols product on-specification in terms of water content.

One will appreciate that an advantage of the present invention is the ability to produce mixed butanols and DIB in a common scheme that can utilize one main fixed bed reactor. In conventional methods, butanols and DIBs can both be prepared from the isobutene in the initial mixed butenes feed stream, but until recently there have not been any butene hydration processes in place that efficiently convert mixed butenes into butanols while, at the same time, dimerizing part of the butene feed into oligomers, such as DIBs.

As mentioned above, the '449 publication addresses this same issue by simultaneously hydrating and oligomerizing mixed butenes to produce alcohols and DIBs. However, the advantage of the present invention over the '449 publication is that the present invention provides greater mechanisms for separating the butanol/DIB products from water (aqueous phase that exits the reactor). Specifically, in certain embodiments, the current invention utilizes a high and low pressure separator, as well as an azeotropic distillation column, which is more adept at separating the desired product from water than conventional methods. Additionally, another embodiment of the present invention integrates a pervaporation membrane to break up the azeotropic water-butanols mixture thereby enhancing separation. In yet another embodiment, a double column entrainer system replaces the azeotropic distillation column, which further enhances the ability of the system to separate the mixed butanols product from the azeotropic mixture.

Another advantage is that the present invention has increased single-pass conversion of butenes to butanols as compared with conventional methods. In one embodiment that is shown in FIG. 5, the present invention utilizes a multi-stage reactor in which mixed butenes are fed to the different stages of the reactor intermittently and product separation modules are installed. The use of a multi-stage reactor significantly increases the single-pass conversion of butenes to butanols because of the increased reaction time due to multiple stages. Additionally, in another embodiment that is shown in FIG. 6, the present invention uses an isomerization unit in which 2-butenes are converted into 1-butenes prior to entering the multi-stage reactor. Because the hydration reaction rate of 1-butenes is significantly higher than that of 2-butenes, the addition of a "2-butene to 1-butene" isomerization unit will further enhance the single-pass conversion rate of the mixed butene feed.

Similarly, the present invention is also improved over conventional methods in that it provides increased butanol yield. This advantage can be achieved in some embodiments through the use of a "2-butene to 1-butene" isomerization unit. In another embodiment, increased butanol yield can be accomplished through the integration of a small fixed bed hydration reactor downstream of the debutenizer. This small hydration reactor allows for the hydration of unreacted butenes removed from the debutenizer, which thereby increases the overall butanol yield of the system.

Another advantage is that the products of the present invention can be used as superior gasoline constituents without separation. The mixed butanols serve as oxygenated octane enhancers to provide for increased combustion efficiency, thereby reducing emissions. The DIBs complement the mixed butanols by serving as high energy content octane enhancers and low RVP gasoline components.

The advantageous qualities of butanols and DIBs as gasoline components compared with other known gasoline components are further explained by the data in Table 1. This data stems from an experiment in which the five compounds listed below (MTBE, ethanol, 2-butanol, t-butanol, and DIB) are each blended into a base gasoline in concentrations of 5, 10, 15, 20, and 25%, respectively, and their respective characteristics are determined. In particular, Table 1 sets forth the trends in RON, Mon, octane sensitivity, and RVP, respectively.

TABLE 1

Blending Properties Comparison for Common Fuel Blends

| Blends | Blending RON | Blending MON | Blending Sensitivity | Energy Density or Higher Heating Value (MJ/Kg) | RVP 15% v/v Blend |
|---|---|---|---|---|---|
| Base gasoline | 85.8 | 81.0 | 4.8 | 45.6 | 9.46 |
| MTBE | 124.7 | 103.5 | 21.2 | 38.0 | 9.6 |
| Ethanol | 139.8 | 106.6 | 33.2 | 29.9 | 11.5 |
| 2-Butanol | 116.6 | 97.8 | 18.8 | 37.3 | 10.4 |
| t-butanol | 108.6 | 89.3 | 19.3 | 37.3 | 9.96 |
| DIB | 132.1 | 99.2 | 32.9 | 48.2 | 8.5 |

As shown by Table 1, compared with other common fuel constituents, DIB has the lowest RVP, the highest energy density, the second highest blending RON, and the second highest blending octane sensitivity (essentially equivalent to that of ethanol). Additionally, 2-butanol and t-butanol have blending octane sensitivities and energy densities comparable to MTBE, and result in a lower RVP at 15% concentrations than ethanol. Based on this data, it can be inferred that the combination of butanols and DIBs creates a high-octane fuel additive with the potential to replace ethanol as a superior oxygenate. The present invention allows for high-yield, on-specification production of a mixed butanols and DIB product through the process scheme described herein.

As mentioned, the alcohols and oligomers in the product stream made in accordance with the embodiment of the present invention can be used as a component in fuel compositions or as a neat fuel composition. For example, in one embodiment, a neat fuel composition can be prepared according to the methods described herein that include a mixed butanol fuel having an octane rating suitable for use in combustion or compression engines. In another embodiment, a fuel composition that includes a fuel component and a mixed butanol fuel is provided. In an embodiment, the fuel component can include jet fuel, gasoline, aviation gasoline, diesel, heating oil, bunker oil, or combination thereof. In an aspect, the mixed butanols can include n-butanol, 2-butanol, iso-butanol, t-butanol, or combination thereof; or alternatively, 2-butanol and t-butanol. In certain embodiments, the mixed butanols can include at least two butanol compounds selected from n-butanol, 2-butanol, iso-butanol, t-butanol, or combination thereof; or alternatively, 2-butanol and t-butanol.

The mixed alcohols (butanols) stream made in accordance with the various embodiments of the present invention can be used in other types of fuel compositions, as will be apparent to those skilled in the art and are to be considered within the scope of the present invention.

As described herein, the process and system of the present invention can be thought of as being, according to one embodiment, a hydration of n-butene isomers (i.e., 1-butene, trans-2-butene, isobutene and cis-2-butene) and a selective oligomerization (dimerization) of at least a portion of the isobutene in the presence of water with the oligomerization and hydration reactions implemented in same reactor in combination with selective downstream separation techniques.

The process and the system of the present invention provide a number of advantages over the conventional hydration and oligomerization/dimerization processes. These advantages include but are not limited to: (1) providing higher purity in the composition of the mixed butanols/DIBs final product than previous methods for simultaneously hydrating and oligomerizing mixed olefin feeds; (2) providing a higher rate of single-pass conversion of the mixed butenes feed to mixed butanols and DIBs; and (3) providing an alternative gasoline oxygenate that possesses comparable RON enhancement properties and higher energy content than MTBE and ethanol, while eliminating the associated compatibility and contamination issues; and (4) utilizing the products of the present invention—namely, mixed butanols and DIBs—as superior gasoline constituents without separation.

EXAMPLES

The following examples are provided to better illustrate embodiments of the present invention. However, it is to be understood that these examples are merely illustrative in nature, and that the process embodiments of the present invention are not necessarily limited thereto.

The first example (Table 2) stems from an experiment conducted at an integrated pilot plant operated at 60 Kg/day capacity having the configuration and characteristics of the system 100 illustrated in FIG. 1. The mixed olefin feed consisted of mixed butanes and butenes in the following approximate percentages: isobutane (1.11%), n-butane (1.97%), 2-trans-butene (23.17%), 2-cis-butene (12.71%), 1-butene (36.46%), and isobutene (23.30%). The water content of the final product 175 is less than the allowed specification of 0.5% wt. The alcohol-water azeotrope recycled from the azeotropic distillation column back to the high-pressure separator contained approximately 55% wt. of water and approximately 45% wt. of mixed butanols. As shown by the results in Table 2 below, this process enabled enhanced recovery of the mixed butanols in the final product and efficient separation of unreacted mixed butenes and water from debutenizer and azeotropic distillation columns.

Table 2 also shows the makeup of the product stream.

TABLE 2

| Stream | Mixed butene feed (120) | Unreacted components (172) | Product Stream (174) | Alcohol-water azeotrope (182) | Recycled water (184) |
|---|---|---|---|---|---|
| | COMPONENTS, wt % | | | | |
| Isobutane | 1.11% | 5.5% | — | — | — |
| n-Butane | 1.97% | 8.2% | — | — | — |
| 2-trans-butene | 23.17% | 35.4% | — | — | — |
| 1-butene | 36.46% | 15.5% | — | — | — |
| Isobutene | 23.30% | 8.1% | — | — | — |
| 2-cis-Butene | 12.71% | 18.8% | — | — | — |
| water | 0.00% | 1.5% | 0.44% | 55.72% | 99.37% |
| T-butanol | 0.00% | 0.9% | 18.9% | 17.21% | 0.25% |
| 2-butanol | 0.00% | 0.0% | 74.2% | 26.25% | 0.35% |
| DIB1 | 0.00% | 0.1% | 0.1% | 0.03% | 0.03% |
| DIB2 | 0.00% | 0.0% | 3.8% | 0.06% | 0.00% |

The second example (Table 3) represents a combination of experimental and simulation data depicting the performance of system 200 with the addition of a pervaporation membrane system immediately upstream of the azeotropic distillation column as shown in FIG. 2. It can be understood from Table 3 below that the pervaporation membrane system successfully removed water from the azeotropic mixture.

TABLE 3

| | Aqueous Phase from Separators (212) | Alcohol-Water Azeotrope (218) | Feed to the Azeotropic Distillation Column (216) | Water Stream Removed from Aqueous Phase in Pervaporation Membrane (214) | Second Product Line (Azeotropic Distillation Column) (184) |
|---|---|---|---|---|---|
| 1-butene | 0.0% | 0.0% | 0.0% | 0.0% | 0.0% |
| 2-cis-butene | 0.0% | 0.3% | 0.1% | 0.0% | 0.0% |
| 2-trans-butene | 0.0% | 0.1% | 0.0% | 0.0% | 0.0% |
| Isobutene | 0.0% | 0.0% | 0.0% | 0.0% | 0.0% |
| 2-butanol | 56.2% | 11.3% | 49.5% | 2.7% | 73.2% |
| T-butanol | 12.0% | 24.0% | 18.6% | 1.0% | 15.2% |
| Oligomers | 9.1% | 27.2% | 17.6% | 0.0% | 11.2% |
| $H_2O$ | 22.7% | 37.0% | 14.1% | 96.3% | 0.5% |

In the third example (Table 4), a combination of experimental and simulation data was used to illustrate the effect of replacing the azeotropic distillation column with a double column entrainer system in which 1,3,5 Trimethyl benzene is used as the entrainer in the contactor column to separate mixed butanols from the azeotropic mixture (as illustrated in FIG. 3). As shown by Table 4, the water content of the dissolved butanols product stream is 0.25% wt., which is less than the maximum allowable water specification of 0.5% wt.

TABLE 4

| Stream | Aqueous Phase from Separators (312) | Entrainer Feed (314) | Unreacted Water Stream from Contactor (316) | Mixed Butanols/DIB stream from Contactor (318) | Dissolved butanols product stream from Solvent Regenerator (322) | Solvent Stream from Solvent Regenerator (324) |
|---|---|---|---|---|---|---|
| | COMPONENTS, kg/hr | | | | | |
| 2-butanol | 0.5956 | 0.0000 | 0.0000 | 0.5956 | 0.5930 | 0.0024 |
| T-butanol | 0.1645 | 0.0000 | 0.0004 | 0.1641 | 0.1641 | |

TABLE 4-continued

| Stream | Aqueous Phase from Separators (312) | Entrainer Feed (314) | Unreacted Water Stream from Contactor (316) | Mixed Butanols/DIB stream from Contactor (318) | Dissolved butanols product stream from Solvent Regenerator (322) | Solvent Stream from Solvent Regenerator (324) |
|---|---|---|---|---|---|---|
| DIB | 0.0909 | 0.0000 | 0.0000 | 0.0909 | 0.0043 | 0.0006 |
| $H_2O$ | 0.1471 | 0.0000 | 0.1471 | 0.0018 | 0.0018 | |
| 1,3,5 Trimethyl benzene | 0.0000 | 6.0000 | 0.0000 | 5.9726 | 0.0000 | 5.9680 |

The fourth example utilizes the exemplary system 100 with the addition of a small fixed bed hydration reactor downstream of the debutenizer as shown in FIG. 4. The small hydration reactor is used to further recover the unreacted butenes by hydrating them to mixed butanols. This embodiment is designed to further enhance the product yield. Table 5, below, represents the effect of space velocity and temperature on the overall product yield using this system. In this example, for Run 1, the reaction conditions were a temperature of 110° C., pressure of 70 bar, and a space velocity of 1.21 hr-1. Typically n-butenes react to form 2-butanol while isobutene predominantly forms t-butanol and DIB. At steady state, the composition of 2-butanol should be analogous to the composition of n-butenes (1-butene, 2-cis-butene and 2-trans-butene).

As per Table 2, stream 120, the total n-butene composition is 72.34% and total achievable 2-butanol composition at equilibrium is around 72% while t-butanol composition is around 15-28% depending on the final composition on DIB's in the product. Isobutene being more reactive than n-butene based on overall reaction rates, it can be inferred that at 110° C., the reaction is far from equilibrium. As the reaction temperature is increased to 150° C. (Run 2), it can be noted that the reaction is moving towards its equilibrium conversion. Similarly, from the results of Runs 2 and 3, it can be inferred that the change in space velocity can be optimized to obtain equilibrium. The reactor 410, based on these results, can be utilized to ensure optimum capture of mixed butenes from the purge stream.

TABLE 5

| Run # | T °C. | P bar | Space Velocity hr−1 | T-butanol | 2-butanol | DIB1 | DIB2 | Ethers | Water |
|---|---|---|---|---|---|---|---|---|---|
| 1 | 110 | 70 | 1.21 | 54.01% | 44.01% | 0.20% | 0.10% | 0.74% | 0.93% |
| 2 | 150 | 70 | 1.34 | 28.75% | 63.27% | 3.42% | 1.23% | 1.98% | 1.35% |
| 3 | 150 | 70 | 1.5 | 17.97% | 70.30% | 3.58% | 0.08% | 2.37% | 0.40% |

The fifth example utilizes a system with a multi-stage reactor with four reactor stages as shown in FIG. 5. Table 6 shows the change in composition of butene isomers and product butanols at each of the four stages of the reactor. Table 7 depicts the conversion of butenes at each stage and the overall single-pass conversion of all isomers of butene. It can be inferred from Table 6 that the multi-stage reactor can result in a substantial increase in single-pass butenes conversion. This increase in single-pass conversion can considerably decrease the recycle of the unreacted butenes and water, resulting in reduced capital costs.

TABLE 6

| | Number of reactor stages | | | | |
|---|---|---|---|---|---|
| | 0 | 1 | 2 | 3 | 4 |
| | Component, mol % | | | | |
| 2-trans-butene | 30.3% | N/A | 36.9% | 38.7% | 37.8% |
| 1-butene | 39.4% | | 34.8% | 33.3% | 35.8% |
| Isobutene | 13.7% | | 6.7% | 5.2% | 4.6% |
| 2-cis-butene | 16.5% | | 19.8% | 21.0% | 20.6% |
| t-butanol | 0.0% | 0.29% | 0.24% | 0.38% | 0.21% |
| 2-butanol | 0.0% | 0.68% | 0.71% | 0.35% | 0.22% |
| $H_2O$ | 0.0% | 0.98% | 0.84% | 1.09% | 0.79% |

TABLE 7

| | Reactor Stages | | | | Overall Conversion |
|---|---|---|---|---|---|
| | 1 | 2 | 3 | 4 | |
| Butene before reaction (area) | 1309 | 1171 | 991 | 871 | 1309 |
| Butene after reaction (area) | 1171 | 991 | 871 | 785 | 785 |

TABLE 7-continued

| | Reactor Stages | | | | Overall Conversion |
|---|---|---|---|---|---|
| | 1 | 2 | 3 | 4 | |
| Single pass Conversion % | 10.54% | 15.37% | 12.11% | 9.87% | 39.96% |

The sixth example stems from an experiment that uses a system with a multi-stage reactor in place of a conventional fixed bed reactor, as well as a "2-butene to 1-butene" isomerization unit as in FIG. 6. Table 8 below shows the difference in the reaction rates of each butene isomer using this system. These results show that isobutene is the fastest reacting butene isomer, while 2-butene is the slowest reacting isomer.

TABLE 8

| Component | Isobutene | 1-butene | 2-cis-butene | 2-trans-butene |
|---|---|---|---|---|
| Total conversion % | 79.48% | 44.00% | 23.35% | 23.15% |
| Total Butene Conversion | | | 39.96% | |

The seventh example stems from an experiment that uses a system with a multi-stage reactor and two conduits used to divert portions of the recycled unreacted butenes back to the high pressure separator and low pressure separator (inner-loop), as shown in FIG. 7. Table 9 below shows the impact of the recycle ratio on the water content in the product. As shown by these results, the water content is decreasing from 0.88 wt % to 0.34 wt % as the recycle flow to the inner-loop increases.

TABLE 9

| Mass Fraction | No Butene Recycle | Recycle to inner loop = 30% of 172 | Recycle to inner loop = 65% of 172 |
|---|---|---|---|
| | | Product Composition, wt % | |
| T-butanol | 28.52% | 28.93% | 29.72% |
| 2-butanol | 65.99% | 65.87% | 65.22% |
| DIB-1 | 2.28% | 2.30% | 2.34% |
| DIB-2 | 1.95% | 1.97% | 2.01% |
| H$_2$O | 0.88% | 0.55% | 0.34% |

While the present invention has been described above using specific embodiments, there are many variations and modifications that will be apparent to those having ordinary skill in the art. As such, the described embodiments are to be considered in all respects as illustrative, and not restrictive. Therefore, the scope of the invention is indicated by the appended claims, rather than by the foregoing description. All changes that come within the meaning and range of equivalency of the claims are to be embraced within their scope.

What is claimed is:

1. A process for simultaneously hydrating and oligomerizing a hydrocarbon feed comprising mixed olefins, the process comprising the steps of:
    introducing the hydrocarbon feed in the presence of water into a fixed bed reactor under reaction conditions that are operable to hydrate the mixed olefins and oligomerize at least a portion of the mixed olefins;
    contacting the hydrocarbon feed with a catalyst within the fixed bed reactor, wherein the catalyst is of the type that hydrates the mixed olefins to form mixed alcohols and oligomerizes at least a portion of the mixed olefins into oligomers to produce a first product stream that includes an organic phase and an aqueous phase;
    introducing the first product stream into a first separator which separates the organic phase from the aqueous phase;
    introducing the separated organic phase into a second separator which separates unreacted olefins from mixed alcohols and one or more oligomers which comprise a final product stream; and
    introducing the separated aqueous phase into a third separator which separates an alcohol-water azeotrope component from waters;
    wherein the mixed olefins comprise mixed butenes including 1-butene, 2-trans-butene, 2-cis-butene, and isobutene and the mixed alcohols comprise mixed butanols;
    wherein the second separator comprises a debutenizer which removes unreacted butenes and the final product stream comprises mixed butanols and DIB.

2. The process of claim 1, further including the steps of adjusting a pressure and temperature of the hydrocarbon feed and adjusting a pressure and temperature of the water.

3. The process of claim 2, wherein a pressure of the fixed bed reactor is between about 10-70 bar, and the temperature of the fixed bed reactor is between about 100-160° C.

4. The process of claim 1, wherein the hydrocarbon feed consists essentially of butenes.

5. The process of claim 1, wherein the first separator comprises a high-pressure separator and a low pressure separator that are arranged in series with the low-pressure separator being downstream of the high-pressure separator, wherein each of the high and low-pressure separators is configured to separate the organic phase from the aqueous phase.

6. The process of claim 1, further including the step of recycling back the unreacted butenes to the fixed bed reactor.

7. The process of claim 1, further including the step of recycling back the unreacted butenes partially to the high pressure separator.

8. The process of claim 1, further including the step of recycling back the unreacted butenes partially to the low pressure separator.

9. The process of claim 5, where the aqueous phase from both the high pressure separator and the low pressure separator are combined prior to being introduced into the third separator.

10. The process of claim 1, wherein the unreacted butenes removed from the debutenizer are transported to a hydration reactor containing a hydration catalyst and in which the unreacted butenes are reacted to form a mixed butanols stream.

11. The process of claim 10, wherein the mixed butanols stream formed in the hydration reactor is recycled back to the first separator.

12. A process for simultaneously hydrating and oligomerizing a hydrocarbon feed comprising mixed olefins, the process comprising the steps of:
    introducing the hydrocarbon feed in the presence of water into a fixed bed reactor under reaction conditions that are operable to hydrate the mixed olefins and oligomerize at least a portion of the mixed olefins;
    contacting the hydrocarbon feed with a catalyst within the fixed bed reactor, wherein the catalyst is of the type that hydrates the mixed olefins to form mixed alcohols and oligomerizes at least a portion of the mixed olefins into oligomers to produce a first product stream that includes an organic phase and an aqueous phase;
    introducing the first product stream into a first separator which separates the organic phase from the aqueous phase;

introducing the separated organic phase into a second separator which separates unreacted olefins from mixed alcohols and one or more oligomers which comprise a final product stream; and introducing the separated aqueous phase into a third separator which separates an alcohol-water azeotrope component from water; wherein the third separator comprises an azeotropic distillation column in which the alcohol-water azeotrope is distilled out of the aqueous phase and recycled back to the first separator and water is recycled back to the fixed bed reactor.

13. The process of claim 12, further including the step of passing the aqueous phase from the first separator transported through a pervaporation membrane for removing water from the aqueous solution, wherein the removed water is recycled back to the fixed bed reactor, and the remaining aqueous solution is introduced into the third separator.

14. The process of claim 13, wherein the third separator comprises an azeotropic distillation column in which the alcohol-water azeotrope is distilled out of the aqueous phase and recycled back to the pervaporation membrane.

15. A process for simultaneously hydrating and oligomerizing a hydrocarbon feed comprising mixed olefins, the process comprising the steps of:

introducing the hydrocarbon feed in the presence of water into a fixed bed reactor under reaction conditions that are operable to hydrate the mixed olefins and oligomerize at least a portion of the mixed olefins;

contacting the hydrocarbon feed with a catalyst within the fixed bed reactor, wherein the catalyst is of the type that hydrates the mixed olefins to form mixed alcohols and oligomerizes at least a portion of the mixed olefins into oligomers to produce a first product stream that includes an organic phase and an aqueous phase;

introducing the first product stream into a first separator which separates the organic phase from the aqueous phase;

introducing the separated organic phase into a second separator which separates unreacted olefins from mixed alcohols and one or more oligomers which comprise a final product stream; and introducing the separated aqueous phase into a third separator which separates an alcohol-water azeotrope component from water; wherein the third separator comprises a double-column entrainer system that includes a contactor column into which an entrainer is injected, and a solvent regenerator column that is located is series with and downstream of the contactor column.

16. The process of claim 15, wherein the aqueous phase from the first separator is first introduced into the contactor column in which mixed alcohols and oligomers are absorbed into the entrainer and are then introduced into the solvent regenerator column in which 1) the mixed alcohols and oligomers are removed and 2) the entrainer is regenerated and recycled back to the contactor column.

17. The process of claim 16, further including the steps of removing water from the mixed alcohols and oligomers in the contactor column, and recycling the water back to the fixed bed reactor.

18. The process of claim 16, wherein the entrainer is 1,3,5 Trimethyl benzene.

19. The process of claim 1, further comprising the step of combining the final product stream with a gasoline stream to produce a gasoline product with reduced Reid vapor pressure (RVP) and increased research octane number (RON) compared with the gasoline stream alone.

20. The process of claim 1, wherein the catalyst present in the fixed bed reactor comprises an ion exchange resin catalyst.

21. The process of claim 1, wherein the fixed bed reactor comprises a multi-stage reactor, with each stage having an individual feed line that receives the hydrocarbon feed and an individual exit line that communicate with a common line that delivers the first product stream to the first separator.

22. The process of claim 1, further including an isomerization unit that is fluidly connected between the second separator and the fixed bed reactor and receives the unreacted olefins from the second separator and serves to convert the unreacted olefins from one isomer to another isomer prior to introduction into the fixed bed reactor.

23. The process of claim 22, wherein the isomerization unit comprises a 2-butenes to 1-butenes isomerization unit and the one isomer comprises a 2-butenes and the other isomer comprises 1-butenes.

* * * * *